(12) United States Patent
Marotzki

(10) Patent No.: US 6,468,788 B1
(45) Date of Patent: Oct. 22, 2002

(54) METHOD AND DEVICE FOR ACCOMMODATING A CELL CULTURE

(76) Inventor: Stefan Marotzki, Pommernstrasse 63, 25436, Tornesch (DE)

( * ) Notice: Subject to any disclaimer, the term of this patent is extended or adjusted under 35 U.S.C. 154(b) by 0 days.

(21) Appl. No.: 09/787,948

(22) PCT Filed: Sep. 13, 1999

(86) PCT No.: PCT/EP99/06762

§ 371 (c)(1),
(2), (4) Date: Mar. 23, 2001

(87) PCT Pub. No.: WO00/17315

PCT Pub. Date: Mar. 30, 2000

(30) Foreign Application Priority Data

Sep. 24, 1998 (DE) .................... 298 17 223 U
Oct. 27, 1998 (EP) .................... 98120337

(51) Int. Cl.[7] .................... C12M 1/22
(52) U.S. Cl. .................... 435/305.1; 435/305.2; 435/305.3; 435/305.4; 435/288.3
(58) Field of Search .................... 435/288.3, 305.1, 435/305.2, 305.3, 305.4

(56) References Cited

U.S. PATENT DOCUMENTS 3,745,091 A * 7/1973 McCormick
4,294,924 A * 10/1981 Pepicelli et al. .............. 435/30
4,634,676 A * 1/1987 Sapatino .................... 435/294

FOREIGN PATENT DOCUMENTS

FR 2698375 * 5/1994

* cited by examiner

*Primary Examiner*—David A. Redding
(74) *Attorney, Agent, or Firm*—Alix, Yale & Ristas, LLP

(57) ABSTRACT

The invention relates to a device for accommodating a cell culture comprising a vessel (1) having a base (3) and walls (4), and comprising a lid (2) which can be inserted into the vessel (1). The lid is provided with an evacuation opening (6) for evacuating displaced air and excess liquid. The evacuation opening can be closed after the lid (2) has been inserted. Inside the vessel (1), devices (31) which are provided on the lid (2) make it possible to form interspaced chambers (30) and to form troughs on said lid (2).

26 Claims, 3 Drawing Sheets

METHOD AND DEVICE FOR ACCOMMODATING A CELL CULTURE

For treating or examining cells in molecular biology or genetic engineering, devices are used which consist, on the one hand, of a vessel (for example a Petri dish) for receiving the cells and a reaction liquid, and, on the other hand, of a cover ("Lab-Tek II" brochure from Nalge Nunc International, Naperville; "EasiSeal" brochure from HYBAID Limited, Teddigton; "Gene Frame" brochure from Advanced Biotechnologies Ltd., Epsom; EP-A 611 598). A distinction must be made here between covers which are simply placed loosely on the upper edge of the vessel and airtight lids which are connected adhesively and airtight to the edge of the device or to a slide forming the base of the device. When the latter covers are applied, care must be taken to ensure that air bubbles are avoided between the lid and the substrate. This is generally done by means of some of the reaction liquid being displaced towards the side as the flat lid is being applied. However, this is only possible if the vessel has no walls. As these are desired in certain process stages, walls are provided which can be tightly connected to and detached from the base (slide) of the device. In the known devices mentioned above, the possibility of removal of the walls is also provided because a substrate layer which is so thin that the temperature changes needed during the process can be effected quickly and with precision control can be easily produced with a flat lid.

Vessels with vertical walls are also known in which a thin substrate layer is produced by means of a cover being lowered partially into the vessel (U.S. Pat. No. 4,294,924; U.S. Pat. No. 4,321,330; DE-A-196 24 917). The thin substrate layer is enclosed between a base of the cover and the base plate of the vessel. The cover is inserted into the vessel, with air and excess liquid being displaced. This makes tight closure difficult.

The invention is based on the object of providing a method and a device which permit the optionally thin-layered substrate to be sealed off even in cases where walls are present. The solution lies in the features of claims 1 and 2.

When the cover is being introduced between the walls of the vessel, the air situated above the substrate in the vessel is displaced through the outflow opening. A possible excess amount of reaction liquid is also displaced through the outflow opening. The cover can be lowered inside the vessel until the desired thickness of the substrate layer is achieved between the base plate of the vessel and the opposite cover base, which desired thickness can range from several hundredths of a millimetre to several millimetres.

In order to avoid undesired clearance, the circumferential surface of the cover can fit closely, with an essentially identical shape, to the internal surface of the walls. This fit can also constitute the sealing of the cover with respect to the walls, for example by means of a ground-glass joint or a plastic seal under elastic pressure. However, this does not need to be the case, since, in addition to a close, but not tight fit of the circumferential surface of the cover to the internal surface of the walls, a special seal can be provided which can cooperate, for example, with the edge of the vessel walls or a shoulder thereof. In these cases it is often expedient to provide a holder for maintaining the sealing position of the cover with respect to the vessel, for example a screw-on, snap or spring closure; however, the tight fit of the cover on the vessel walls can also be self-supporting, for example as a result of the frictional forces which exist between two ground-glass surfaces.

It is expedient for the lower surface of the cover base to extend approximately parallel to the base of the vessel in order to be able to achieve an essentially constant layer thickness. The cover and the vessel can be provided with -cooperating contact surfaces which define the size and constancy of the layer thickness.

The outflow opening can be provided with a closure device. However, the possibility also exists of providing sealing by means of a subsequently applied oil layer. This also applies to the circumferential sealing. In many cases a tight seal is only required in respect of the external atmosphere in order, for example, to avoid evaporation or the admission of oxygen. In these cases it may suffice if the seal is formed not on the vessel and cover, but is instead formed by an apparatus which receives the device, for example a type of autoclave in which there is an internal atmosphere which is chosen in accordance with the intended purposes. To avoid evaporation, for example, it can have sufficient moisture. To avoid admission of harmful gases, it can consist of nitrogen or noble gas.

To ensure that it is not only the air in the area of the outflow opening that is removed, but also that air quantity which may be contained between the circumferential surface of the cover and the vessel walls, it is possible for the outflow opening to be provided with an ascending section whose mouth is at least approximately level with the upper end of the gap situated between the circumferential surface of the cover and the vessel walls. On slow insertion of the cover into the vessel, the static pressure of the liquid column present in the ascending section of the outflow opening then ensures that the air in the circumferential gap is also displaced.

When the cells have deposited sufficiently firmly on the base of the vessel, the excess liquid can be readily drawn off or displaced through the outflow opening without any risk of losing cells. So that it is also possible to work with cells which are in suspension, the outflow opening can be provided with a screen which holds back the cells during displacement of the liquid.

A plurality of openings can be provided which are designed for attachment of an admission and discharge line for a medium. One or more of these openings can serve as outflow opening. The device can then also be used as a so-called reactor (Meenen et al.; "Semi Continuous Reactor System . . . ", Poster 1994 Biomaterials 21:905–908).

The cells involved can be adherent cells which stick to the base of the cell culture dish, or suspension cells which swim in the culture medium. Alternatively, tissue sections can also be cultured in the dish. In general, both eukaryotic and prokaryotic cells can be cultured in the vessel. Treatments and examinations which can be carried out using the device according to the invention can, for example, be all types of in situ hybridization and in situ PCR.

The outflow opening is expediently provided inside the cover, at a distance from the edge of the latter. However, this does not exclude the possibility of its being formed by means of a spacing provided, at least in places, between the edge of the cover and the vessel walls. A particularly advantageous design in this connection is one in which the edge of the cover comprises a collar which rises upwards from the bottom of the cover plate, which forms in its entirety or in places the said spacing for forming an outflow opening, and whose upper edge cooperates with the vessel walls to form a seal. As the cover is being lowered, quantities of gas and liquid enclosed between cover and vessel can then escape, and it is only at the end of this procedure, when the cover reaches its end position, that the seal is obtained.

If the intention is to subject a plurality of cultures to the same thermal conditions, it is expedient to connect a plurality of vessels to one another. In this case, a cover of the type indicated above can be provided for each one of the vessels. However, it is also possible to connect a plurality of covers to one another for joint actuation. It is of course possible to make the walls of a plurality of vessels integral with one another, in which case either the bases are also connected in one piece with the walls or they can be separated from these, for example in the form of a slide.

Of particular importance, however, in the context of the invention is the possibility of being able to create a plurality of chambers by means of forming walls inside one and the same vessel, which chambers, during the course of treatment of a culture, are at times separated from one another, or are not separated, depending on the requirements. For this purpose, the cover is provided with an arrangement for dividing off such chambers from one another. A particularly advantageous design is one in which a narrower vessel is so designed that it can be accommodated in a wider vessel. The cover of the wider vessel is in this case generally designed in such a way that it serves solely to close the area of the wider vessel situated outside the narrower vessel. For the closure of the narrower vessel, a special closure is then optionally provided, for which the general comments made above in respect of the closure of the vessels also apply. This means that in addition to a simple air-permeable or airtight closure, a cover can also be provided which is equipped with an opening for displacement of the atmosphere, and possibly excess liquid, arising in the narrower vessel, and whose air opening can be closed. However, there is also the possibility of structurally connecting the covers of the wider vessel and of the narrower vessel to one another for joint actuation.

Where, in the present connection, mention is made of "a" narrower vessel, this is intended to mean that it is at least one; a plurality of narrower vessels can also be provided, however, in a wider vessel. The arrangement of a narrower vessel in a wider vessel affords the possibility of subjecting the cultures within the narrower vessel and within the wider vessel to exactly the same thermal conditions. They can have separate bases. Of particular importance, however, is a design in which the narrower vessel shares the base with the wider vessel. This affords the possibility of subjecting one and the same culture inside the wider vessel to different reaction conditions (for example another reaction liquid) during all or some of the reaction steps. Accordingly, the wall of the narrower vessel is used only in those reaction steps, inside the otherwise uniform culture, in which the reaction conditions are intended to be different, e.g. for positive control or negative control in PCR.

There are cases in which the narrower vessel can remain in the wider vessel during the entire reaction or sequence of reactions. In these cases, it can be permanently connected to the base and to the wider vessel from the outset at the factory stage. In other cases, the compartmentalization is desired at the start of the reaction or chain of reactions; the narrower vessel can then be connected, likewise at the factory stage, to the base of the wider vessel, but it can be detached therefrom so that the compartmentalization can be annulled at the desired time. The factory-stage arrangement has the advantage that the narrower vessel can be accurately positioned in relation to the walls of the wider one, and this therefore guarantees that the cover fits. In other cases, one will want to have the freedom to be able to carry out the compartmentalization at any desired time. In these cases, the wall of the narrower vessel can be fitted by the user.

If the cover is intended to close off the wider vessel completely, it must not only have its circumferential surface adapted to the wall of the wider vessel, but must also be able to be connected sufficiently tightly to the narrower vessel. This can be achieved by its having a cutout which is adapted to the shape of the narrower vessel and which can join to the latter with the desired tightness. This cutout can be formed by an outflow opening. In another embodiment, the cover is connected in one piece to the wall of the narrower vessel, so that the compartmentalization made possible by the narrower vessel comes about with the insertion of the cover. In both cases, the cover serves as a holder or guide during insertion and, if appropriate, also during use of the narrower vessel.

In some cases an absolutely tight seal between the wall of the narrower vessel and the base of the wider vessel is not necessary; the narrower vessel can then simply be formed by a small tube which is held by the cover and reaches down to the base of the wider vessel. If a tight connection of the narrower vessel wall against the base is required, the lower edge of the wall of the narrower vessel can be provided with a seal, the wall being pressed against the base by the cover or an additional clamp in order to generate the sealing pressure. The wall of the narrower vessel can also be bonded to the base. In the simplest case, the vessel wall of the narrower vessel consists of a sealing ring which is fitted between the base plate and the cover base, fits tightly against these and divides the chamber enclosed by it from the space surrounding it. To ensure that the enclosed chamber can be subjected to a different treatment, it must be accessible by way of a cover opening which is located in its area and which can be the outflow opening.

According to the invention, the cover can also be provided with further arrangements which are desired for the treatment of the cultures. For electroporation, the cover and the base can support electrodes, for example planar electrodes, and the cells to be treated are arranged on a porous membrane between these.

If displaced liquid is to be collected, or if a reservoir of liquid is to be formed which is intended to replace the liquid present in the treatment chamber, a trough can be formed on the upper side and communicate with a corresponding opening in the cover. For liquid which is to pass into the treatment chamber by diffusion or flow, the trough base should not be lower than the mouth of the opening. A plurality of openings can be provided per vessel in order to permit liquid exchange by flow. For this purpose, a plurality of openings should be provided, of which at least one is connected to a trough which is separate from the trough or troughs of the other openings and which is not deeper than the mouth of the opening.

Particularly with respect to machine treatment of the devices, it may be expedient to combine a plurality of vessels and provided them with a common cover which has the requisite openings in the area of each individual vessel.

For machine treatment, a machine is provided which is equipped with means for introducing at least one liquid into at least one of the troughs or openings. It can also be designed for suctioning liquid from a trough or opening.

In this context, the term trough is intended to signify any vessel-like depression without stating its width or height, unless such a statement is expressly made. The subjects of claims 23 to 26 and of FIGS. 12 to 16 serve for protection independently of claims 1 to 22.

The invention is explained in greater detail below with reference to the drawing, which diagrammatically depicts advantageous illustrative embodiments, and in which.

Figure 3:
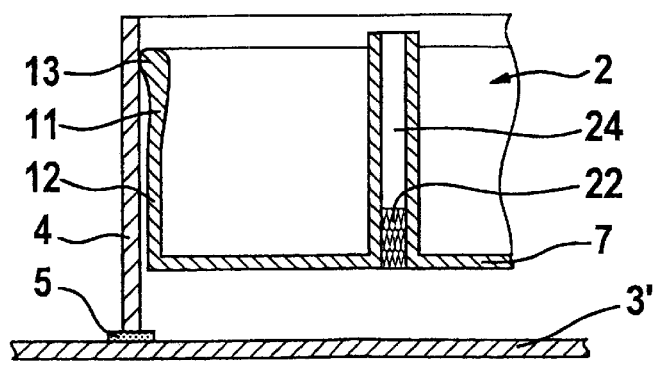
FIG. 3 shows a device with elastically sealing cover.

The device basically comprises the vessel 1, for example a Petri dish, and a cover 2. The vessel 1 has a base plate 3 and walls 4. These can be designed in one piece or as multiple parts. FIG. 3 indicates that the base plate is formed by a slide 3' on which the walls 4 are secured in a known manner by means of a releasable adhesive 5. Instead of this, a sealing ring can be used in conjunction with an arrangement for holding the walls, with inclusion of the sealing ring on the slide. Vessel and cover are made of a material which does not negatively affect the substrate and the process that may be carried out, for example glass or suitable plastic. The vessels may be individual vessels; alternatively, a plurality of vessels are provided contiguously as one group.

In some work phases, the dish 1 may be used without the special cover 2, for example open, or with a lid placed flat on top. If the intention is to subject the cells in the dish to molecular biological or genetic engineering treatments or examinations, the cover 2 according to the invention can instead be used, which cover 2 closes the dish off tightly against the walls 4. It has an opening 6 which is referred to in the claims as an outflow opening, because the atmosphere which is displaced upon insertion of the cover into the vessel can flow off through this opening. To ensure that the air is removed without any being left, it is generally also necessary here to displace some of the liquid. The outflow opening is therefore dimensioned in such a way that this is possible. Its lower mouth is arranged in that part of the cover base 7 submerged in the liquid, and in fact it is preferably arranged in the highest region thereof. The distance between the bottom surface of the cover base 7 and the top 8 of the base generally amounts to 20 μm for observation purposes, but can also be substantially larger or smaller, depending on requirements. If so required, the outflow opening can be closed after the cover has been applied.

Figure 2:
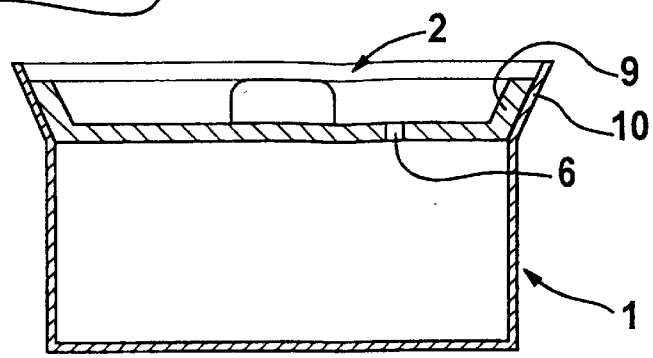
FIG. 2 shows a device with ground-in cover.

The type of sealing of the cover 2 with respect to the walls 4 which is chosen in each particular case depends on the material that has been chosen. If glass is used, this can be achieved by means of grinding. This is illustrated in FIG. 2. The cover 2 and the vessel 1 are provided with collars 9, 10 which have been ground to match and complement each other. The outflow opening 6 is situated at a suitable location within the cover area surrounded by the collar. Such a shape of the vessel and of the cover can also be used with materials other than glass.

If elastically yielding plastic material is used for the vessel walls and/or the cover, the sealing can be achieved by resilient pressing of a sealing edge, as is indicated in FIG. 3. The walls 4 of the vessel, made of glass or plastic for example, extend parallel to one another and perpendicular to the base 8, for example cylindrically. The cover 2 is made of an elastic plastic. Jutting upwards from its preferably flat cover base 7 there is a collar 11 which, in the lower area 12, extends approximately parallel to the walls 4 and, with respect to the latter, has no clearance space or only a slight clearance space. The upper edge 13 of the collar 11 has a slightly greater diameter so that it is elastically compressed upon insertion into the wall 4 and thus bears tightly and with prestressing against the inner surface of the wall 4 about its entire circumference. The position of the cover in the vessel is secured by means of its friction on the vessel walls.

Figure 4:
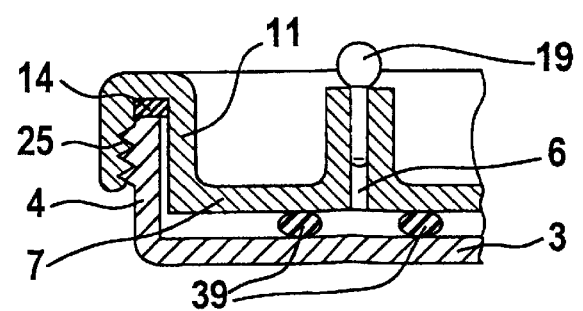
FIG. 4 shows a device with a screw-on cover.

In the illustrative embodiment according to FIG. 4, the collar 11 of the cover likewise adjoins the walls 4 of the vessel with only a slight gap width. At the free edge, the collar 11 and the walls 4 are provided with a cooperating thread 25. A sealing ring 14 is placed between the end faces of these parts. The ring 39 placed between the base plate 3 and the cover base 7 is discussed in detail below.

Figure 5:
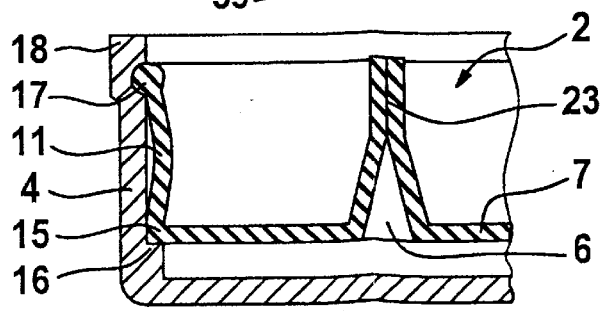
FIG. 5 shows a device with a snap-locking cover.

Instead of the screw-on closure, it is possible to provide any type of snap closure, or a clamp acting from outside on the cover and holding it in its position. A design with a snap closure is illustrated in FIG. 5. The edge 15 of the cover base 7 sits sealingly on a shoulder 16 of the wall 4. It is held in this position by virtue of the fact that the free edge 17 of the collar 11 of the cover 2 cooperates in a locking manner with a circumferential nose 18 on the free edge of the vessel walls. The shoulder 16 also has the advantage that it forms a limit stop which ensures the desired spacing between the cover base 7 and the vessel base 3.

Figure 1:
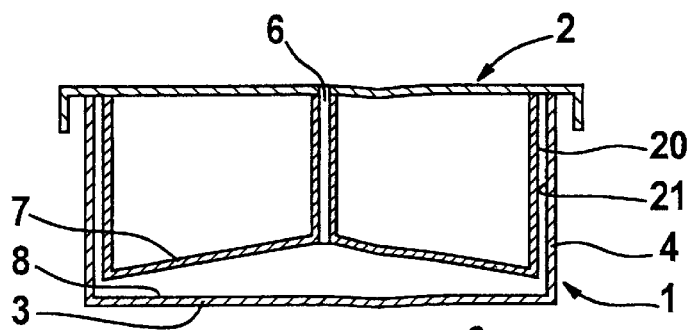
FIG. 1 shows a schematic representation.

As is shown in FIG. 1, the cover base 7 can be shaped in such a way that the outflow opening 6 begins at an elevated part of the base. This makes it easier to eliminate air bubbles without leaving any behind. In general, however, this is not necessary. Remaining air inclusions can be flushed out with an excess of the culture medium or the reaction liquid.

In the examples according to FIGS. 1, 3 and 4, the outflow opening 6 is connected to an ascending tube 24 which is at least as high as the outflow section for removing air from the gap between the cover collar 11 and the vessel walls 4. By means of the static pressure in the ascending tube, it is possible, if so desired, to ensure that air inclusions are driven out from the annular gap between the circumferential surface 20 of the cover and the internal surface 21 of the vessel walls. This objective can also be achieved by giving the outflow opening such a high flow resistance with respect to liquid, and by inserting the cover so quickly, that the overpressure produced in the vessel guarantees the removal of any air from the annular gap. FIG. 5 shows that the outflow opening 6 narrows towards the top to form a gap 23 of small width which as throttle has a correspondingly high flow resistance. This gap can be designed in such a way that, upon insertion of the cover into the vessel, it opens in the manner of a nonreturn valve, with elastic deformation of the material, to allow the escape of the air and excess liquid and, thereafter, under the elastic restoring force of the material and/or under the action of a clamp (not shown in the drawing), once again closes in an airtight manner. By contrast, FIG. 4 shows a stopper 19 for closing the outflow opening. It is also possible, however, to close the opening by means of a droplet of oil.

If there is a danger of cells being swept out with the displaced liquid, the outflow opening 6 is closed by a screen 22, as is indicated diagrammatically in FIG. 3.

A plurality of openings in the nature of the outflow openings 6 can be provided if the intention is to use the device as a bioreactor through which a reaction medium is to pass. In such a case, at least one opening is connected to a liquid admission line and at least one other opening is connected to a liquid discharge line.

The arrangement of an outflow opening within the surface area of the cover has the advantage that it can be easily closed and that the displaced liquid emerges at a defined location, at which it can be taken off with a pipette, for example. However, it is also possible to provide the outflow opening in the interspace between the cover edge and the walls of the vessel. Whereas it was stipulated above that the cover edge closely adjoins the vessel walls for the purpose of guiding or sealing, a sufficient spacing is provided at this location to form an outflow cross section. This spacing can be provided about the entire circumference or else only at one or a few locations.

The arrangement of the outflow opening between cover edge and vessel walls does not rule out a tight seal being created between these. For example, in the illustrative embodiment in FIG. 3, the outflow tube 24 can be dispensed with if a sufficient outflow spacing with respect to the vessel walls 4 is provided in the lower area 12 of the cover collar 11. Upon insertion of the cover 2 into the vessel 1, the enclosed air and excess liquid can flow off through this circumferential spacing. Only when the sealing edge 13 reaches the vessel walls 4 is the outflow inhibited, but not completely excluded, since the sealing edge 13, as a function of the prestressing with which it bears on the vessel walls 4, can lift sufficiently from the vessel walls under the internal overpressure in the manner of a nonreturn valve in order to permit a further outflow. It is only when the force effecting the insertion movement of the cover terminates that the edge bears tightly on the vessel walls.

In the illustrative embodiment in FIG. 4, the outflow opening 6 can be dispensed with if the spacing between the cover collar 11 and the vessel walls 4 and between the cooperating threaded surfaces 25 is great enough to permit outflow. This finishes only when the cover reaches the desired end position and the sealing ring 14 bears on the upper edge of the vessel walls 4.

In some cases it is possible to dispense completely with an airtight closure between the cover edge and the vessel walls, namely if an innocuous atmosphere is guaranteed inside an apparatus receiving the device and if this atmosphere is protected from the external atmosphere by means of an appropriate closure of the apparatus, which in this case replaces the closure provided on the device itself.

Figure 6:
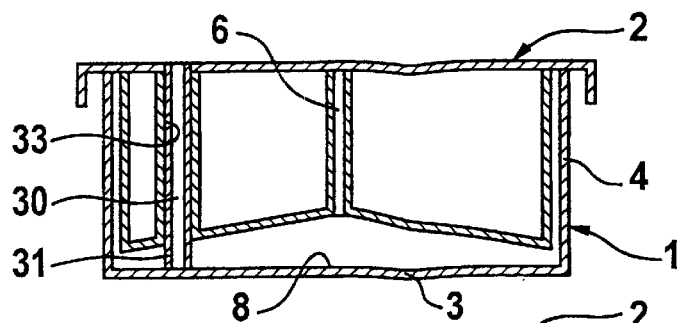
FIGS. 6–8 show different embodiments of a compartmentalized device.
Figure 7:
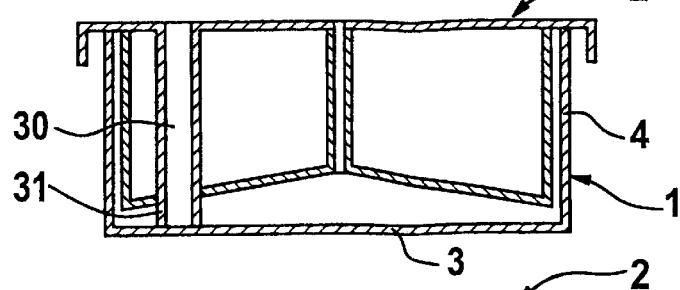
Figure 8:
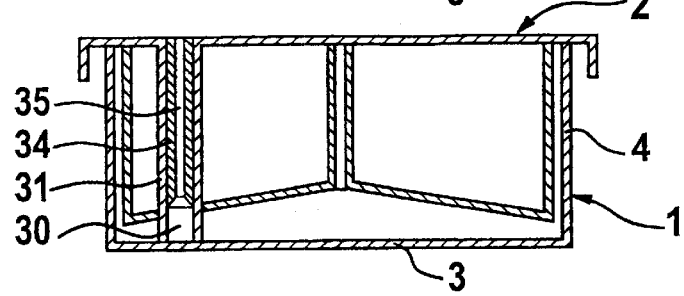
Figure 9:
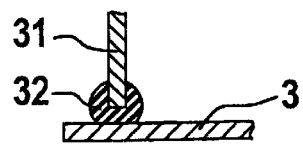
FIG. 9 shows a partial section illustrating one sealing possibility.
Figure 11:
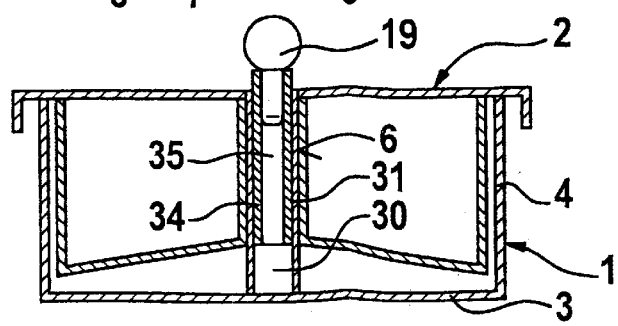
FIG. 11 shows a further compartmentalized device.

The illustrative embodiments according to FIGS. 6 to 8 are based on the illustrative embodiment according to FIG. 1, although they could readily start from any other embodiment of the invention described above. They illustrate the formation of a narrower chamber 30 inside a wider vessel 1. The walls 31 forming the chamber 30 can involve a simple tube, for example made of glass or plastic, and in any case sit with their lower ends on the top 8 of the base plate 3 in order to separate the chamber 30 from its surroundings. If the wall 31 is not designed in one piece with the base plate 3, it can be attached thereto by means of a suitable seal. The seal can be formed by an adhesive or, in accordance with the example shown in FIG. 9, by an elastomer strip 32 placed firmly and sealingly on the lower edge. In some cases it suffices if the lower edge of the wall 31 is placed on the top 8 of the base 3 without an additional sealing means. In this case, and also when using an elastomer seal which is not adhesively bonded, it is expedient to promote the tight contact on the top 8 of the base by means of the wall 31 being prestressed against the base 3. When it is made in one piece with the cover 2, as in FIG. 7, this prestressing can be produced by utilizing the elastic properties of the vessel or cover, by means of the fact that the length of the wall 31 has a certain overdimension with respect to the base spacing of the cover and the cover is placed firmly on the vessel 1, for example with the aid of a screw-on, friction-type or snap closure. However, such presttessing can also be produced if, as in the illustrative embodiment according to FIG. 6, the wall 31 is held releasably in a recess or holder 33 of the cover 2, with a certain frictional force being exerted on the wall 31 by the holder 33. The holder 33 expediently encloses the wall 31 tightly. It is formed, for example, by a bore in which the tubular wall 31 is guided with a close fit. As FIG. 11 shows, this bore can be formed by an outflow opening 6.

If the cover 2 and the wall 31 are separate parts, they must be positioned exactly in relation to one another in the vessel 1. This is most easily done by first inserting the wall 31 into the cover 2 and then inserting the latter, together with the wall, into the vessel 1. Alternatively, the cover is first put into place and the wall 31 is then inserted through the cover. If it is necessary to install the chamber 30 inside the vessel 1 before the cover 2 is put into place, it is best to use a positioning gauge for the wall 31, the dimensions of which positioning gauge in relation to the vessel 1 are the same as those of the cover 2. This positioning gauge can be removed before the cover 2 is inserted, for example after an adhesive connecting the wall 31 to the top 8 of the base has hardened, or the positioning gauge remains in place underneath the cover 2 when the latter is inserted. In this case, the positioning gauge does not need to be a separate part; rather, it can be structurally connected to the wall 31, for example by means of the latter having a series of arms protruding all around from it, parallel to the base 3 of the vessel 1 or to the base 7 of the cover, which arms terminate in positioning contact against the internal surface 21 of the vessel walls 4.

In the same way as the vessel 1 is provided with a cover 2 equipped with outflow arrangement 6, the chamber 30 can be provided with a closure member 34 which is suitable for limiting the height of the substrate above the vessel base 8 and which contains an outflow channel 35 which in turn can be closed by means of a stopper (not shown).

A further example of compartmentalization is illustrated in FIG. 4. A sealing ring 39 of elastomer material, for example a commercially available O-ring, is placed between the base plate 3 and the cover base 7. The ring material is so thick that, in the end position, it bears with elastic deformation tightly against the base plate 3 and the cover base 7. In this way a chamber is created within the sealing ring, which chamber is separated off from the area located outside the sealing ring. It is accessible via the outflow opening 6 in the cover, or via any other opening created especially for this purpose, in order to permit a treatment of its contents which differs from the treatment in the surrounding area. The ring 39 can be placed loosely in the vessel 1 before the cover 2 is put into place, in which case care must be taken to ensure that the area enclosed by it lies at the point where the opening 6 is expected. In order to ensure communication with the opening 6 and to simplify the handling, the ring can also be firmly connected to the cover 2 permanently or temporarily, for example by means of an adhesive or a form-fitting holder (not shown in the drawing).

The compartmentalization according to the invention makes it possible, in individual reaction steps or in a plurality of reaction steps, to do something inside the chamber 30 that is different from what is being done outside it, but with the thermal conditions remaining the same. The cultures can also be the same if the chamber 30 is inserted only after the culture has been placed in the vessel 1. For example, in one stage of a multi-stage procedure, twice as much enzyme can be introduced inside the chamber 30 as is introduced outside the chamber. Thereafter, the chamber wall 31 is removed, and all the cells are once again treated identically. If a plurality of such insert chambers 30 are used in a vessel, the possible variations multiply accordingly.

Figure 10:
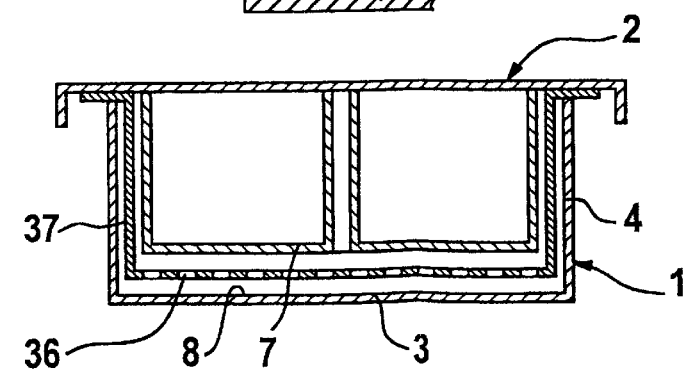
FIG. 10 shows a device with electrode.

If the cells in the vessel are to be subjected to electroporation or electrofusion, metal electrodes (not shown in the drawing) are provided in the cover and base. As is shown in FIG. 10, the cells are then placed on a porous base 36 or a membrane of a cell culture insert 37 between base 3 and cover 2 and are exposed to an electric field.

Figure 12:
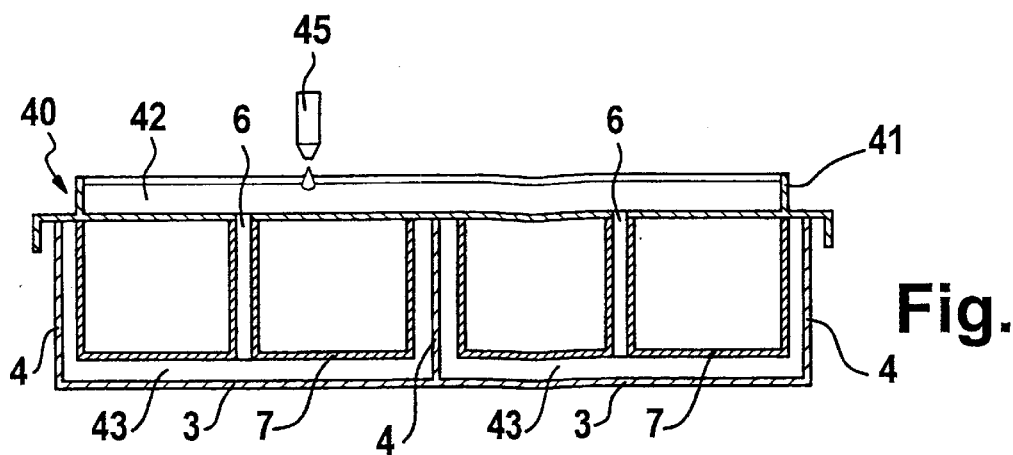
FIG. 12 shows a device with a plurality of vessels and a common cover.
Figure 13:
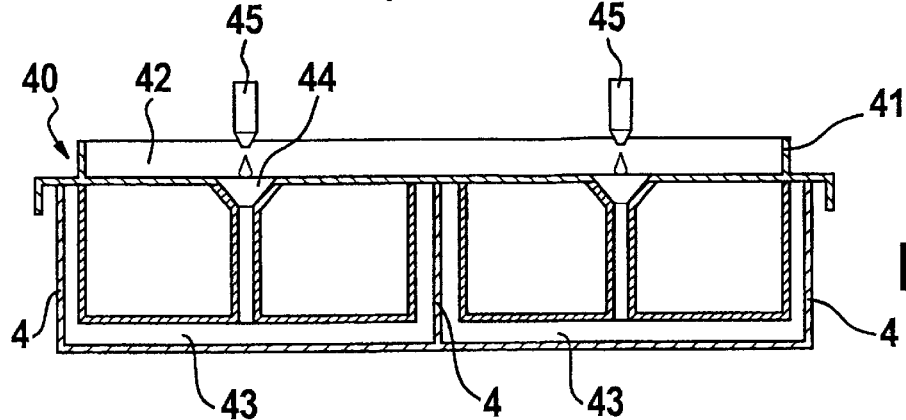
FIG. 13 shows the device according to FIG. 12 with special recesses at the cover openings.
Figure 14:
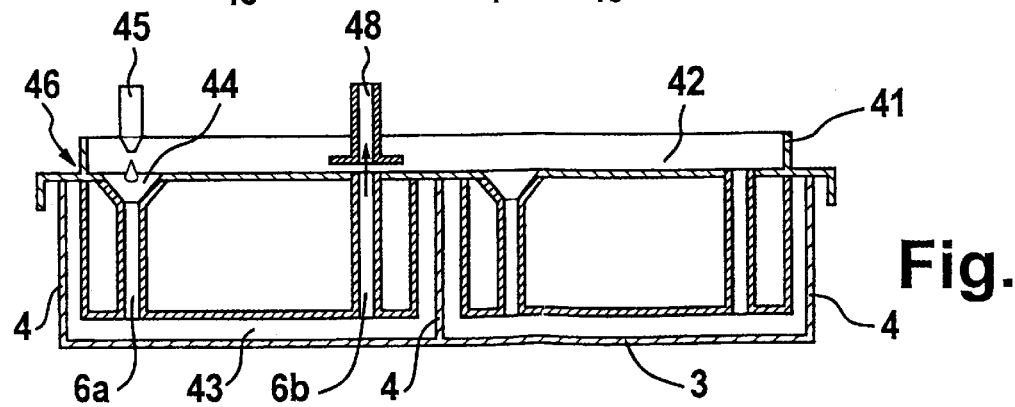
FIG. 14 shows the device according to FIG. 12 with a plurality of openings per vessel.

In the embodiments shown in FIGS. 12 to 14, a plurality of vessels with base 3 and walls 4 are combined in one piece. It is possible for this to include more than the two vessels shown. A common cover 40 is provided for a plurality of these vessels and it cooperates sealingly with the walls 4 of the vessels, in one of the ways explained above. In the embodiments according to FIGS. 12 and 13, an outflow opening 6 in the cover 40 is provided for each vessel.

In the embodiment according to FIG. 12, the cover 40 has, on its upper side, an upwardly projecting edge 41 which delimits a trough 42 into which the outflow openings 6 open. On the one hand, this trough collects the liquid which flows off when the cover is inserted into the vessel. On the other hand—and this is the more important point—the trough can be used for adding liquid which is to be transferred into the treatment chambers 43 in order to modify the properties of the liquid which is present there and in which the cells are situated. It is possible to fill and empty the trough using a suitable known pipetting robot.

The liquid present in the trough 42 can move through the openings 6 and into the chamber 43 by diffusion. A common trough 42 for a plurality of openings 6 of different treatment chambers 43 is chosen if the liquid in the different treatment chambers 43 is to be modified in the same way.

If the treatment liquid in adjoining treatment chambers 43 is to be modified in a different way, separate troughs are used. For example, in the embodiment according to FIG. 12, a further wall 41 (not shown) could be also provided on the upper side of the cover in the middle between the mouths of the openings 6. The embodiment according to FIG. 13 achieves this aim in a slightly different way. A depression 44 in the base of the trough 42 is provided in the mouth area of each of the openings 6. Different liquids can be introduced into the depressions 44 and then in each case diffuse into the associated treatment chambers 43. In the claims, the depressions 44 are also referred to as a trough.

The troughs make it possible to automate the process steps for exchanging the treatment liquid. For this purpose, a suitable machine (for example a known pipetting robot) is provided, with nozzles indicated diagrammatically at 45, which are controlled by a program in such a way that at a given time they introduce a liquid of a desired type and amount into corresponding troughs.

If exchange of the treatment liquid by diffusion takes too long, the treatment liquid can also be exchanged by forced flow. Two illustrative embodiments of devices which are suitable for this are shown in FIGS. 14 to 16.

In FIG. 14 it has been assumed (as in FIGS. 12 and 13) that a plurality of vessels with treatment chambers 43 are combined in one piece and are provided with a common cover 46. Each part of the cover 46 allocated to a vessel has two openings 6a, 6b which open into a trough 42 on the upper side of the cover. At least the opening 6a is provided at the upper end with a depression 44. If so desired, the cover can also be used for exchanging the treatment liquid by diffusion, but it is mainly suited for forced exchange of the treatment liquid. First, the new treatment liquid to be added is introduced into the depression 44 of the opening 6a by means of a nozzle 45 (which may belong to a pipette robot). The treatment liquid present in the treatment chamber 43 is then suctioned off by means of a pipette robot or by means of a suction nozzle 48 lowered onto the other opening 6b, by which means the new liquid to be added is at the same time drawn into the treatment chamber free from bubbles. The amount suctioned off is precisely dosed to guarantee exchange. The new liquid to be introduced can be present in excess if the aim is to achieve as complete as possible a replacement of the liquid previously present in the treatment chamber 43, and if this liquid is to be flushed out by the replacement liquid.

Figure 15:
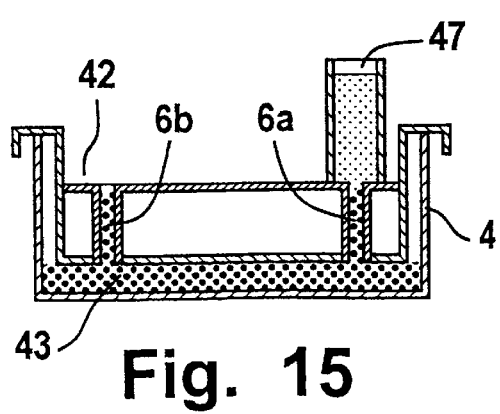
FIGS. 15 and 16 show a vessel with a plurality of openings in various stages of operation.
Figure 16:
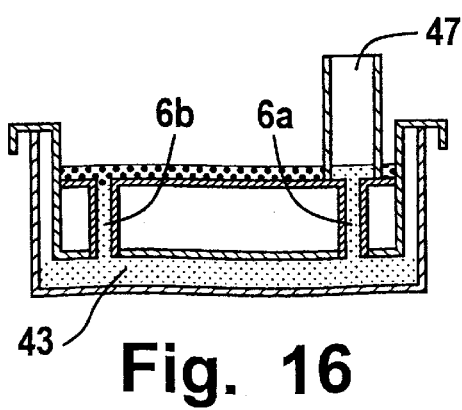

The illustrative embodiment according to FIGS. 15 and 16 permits flow exchange of the liquid without mechanical means. The opening 6a through which new liquid is to be delivered is connected at the top to a trough 47 of small cross section and comparatively great height, while the opening 6b, through which the liquid to be replaced is expelled, communicates with the trough 42 of large cross section and comparatively low height. If, as is shown in FIG. 15, the high trough 47 is filled with the new liquid to be introduced, which is shown by dots, the static pressure difference in the troughs 47 and 42 results in the expulsion of the liquid present in the treatment chamber 43, and symbolized by small circles. According to FIG. 16, the exchange is completed when the levels in troughs 42 and 47 are equal.

It will be appreciated that more than two openings can be provided. For liquid exchange which is as complete as possible, it may be expedient to provide the opening 6a for the new liquid in a central position and to distribute a greater number of outlet openings uniformly near the circumference.

The exchange of liquid can also be carried out in the reverse order by means of the fact that the new liquid to be introduced is introduced at excess pressure into one of the openings and the liquid to be replaced is thereby displaced from the other opening. In this case it may be expedient to design the outlet openings, corresponding to the example in FIG. 5, so as to open under excess pressure and to automatically reclose.

What is claimed is:
1. Device for receiving a liquid containing a cell structure, comprising a vessel including:
   a base plate;
   walls rising upwards from the base plate; and
   a cover which is lowered into the vessel with displacement of air and, where appropriate, excess liquid, the cover having
      an outflow opening and
      an arrangement for closing off the outflow opening from the atmosphere.
2. Device according to claim 1 wherein the circumferential surface of the cover fits closely, with an essentially identical shape, to the internal surface of the walls.
3. Device according to claim 2 wherein the circumferential surface of the cover cooperates closely with the internal surface of the walls.
4. Device according to claim 1 further comprising a seal disposed between the edge of the cover and the edge or a shoulder of the vessel walls.
5. Device according to claim 1 further comprising a holder for maintaining the sealed position of the cover in relation to the vessel.
6. Device according to claim 1 wherein the lower surface of the cover base extends approximately parallel to the base plate of the vessel.
7. Device according to claim 1 wherein the outflow opening is provided with a screen.

8. Device according to claim 1 wherein the outflow opening has an ascending section whose mouth is at least approximately level with the upper end of a gap situated between the circumferential surface of the cover and vessel walls.

9. Device according to claim 1 further comprising at least one cell culture insert.

10. Device for receiving a liquid containing a cell structure, comprising a vessel including:
- a base plate formed by a slide;
- walls rising upwards from the base plate and tightly connected to the slide; and
- a cover which is lowered into the vessel with displacement of air and, where appropriate, excess liquid, the cover having an outflow opening.

11. Device for receiving a liquid containing a cell structure, comprising a vessel including:
- a base plate;
- walls rising upwards from the base plate; and
- a cover which is lowered into the vessel with displacement of air and, where appropriate, excess liquid, the cover having
  - a cover plate,
  - a cover edge including
    - a collar which rises upwards from the cover plate and
    - an upper edge which cooperates with the vessel walls to form a seal; and
  - an outflow opening formed by a spacing provided at least in some places between the cover edge and the vessel walls.

12. Device for receiving a liquid containing a cell structure, comprising a vessel including:
- a base plate;
- walls rising upwards from the base plate;
- a cover which is lowered into the vessel with displacement of air and, where appropriate, excess liquid, the cover having an outflow opening; and
- an arrangement for dividing off a plurality of separate chambers inside the vessel.

13. Device for receiving a liquid containing a cell structure, comprising
- a wider vessel;
- a narrower vessel arranged in the wider vessel;
- wherein the wider vessel includes a base plate, walls rising upwards from the base plate, and a cover which is lowered into the wider vessel with displacement of air and, where appropriate, excess liquid, the cover of the wider vessel having an outflow opening and being designed solely to close the area of the wider vessel situated outside the narrower vessel.

14. Device according to claim 13 wherein the cover has a cutout adopted to the circumference of the narrower vessel.

15. Device according to claim 14 wherein the cutout is formed by the outflow opening.

16. Device according to claim 13 wherein the cover is designed as a holder for the narrower vessel.

17. Device according to claim 16 wherein the cover is connected to the narrower vessel for joint handling.

18. Device according to claim 13 further comprising a cover for the narrower vessel which is separate from the cover of the wider vessel.

19. Device according to claim 13 further comprising a cover which closes both the wider vessel and the narrower vessel.

20. Device according to claim 13 further comprising a ring enclosing a separate chamber disposed between the base plate and the cover base, and the cover has an opening in the area of this chamber.

21. Device for receiving a liquid containing a cell structure, comprising a vessel including:
- a base plate;
- walls rising upwards from the base plate; and
- a cover which is lowered into the vessel with displacement of air and, where appropriate, excess liquid, the cover having
  - an outflow opening defining a mouth and
  - an upper side defining a trough surrounding the mouth of the outflow opening.

22. Device according to claim 21 wherein the trough base is not lower than the associated mouth of the opening.

23. Device according to claim 21 further comprising a plurality of openings, of which at least one is connected to a trough which is separate from the trough or troughs of the other openings and which is not deeper than the mouth of the opening.

24. Device according to claim 21 further comprising a plurality of vessels the cover being common to all of the vessels, the trough having openings in the area of the plurality of vessels.

25. Device according to claim 23 further comprising means for introducing at least one liquid into at least one of the troughs or openings.

26. Device according to claim 25 further comprising at least one means for suctioning liquid out of at least one opening.

* * * * *